United States Patent [19]

Halm et al.

[11] Patent Number: 4,946,980

[45] Date of Patent: Aug. 7, 1990

[54] PREPARATION OF ORGANOSILANES

[75] Inventors: Roland L. Halm, Madison; Kirk M. Chadwick, Hanover, both of Ind.; Brian R. Keyes, Salt Lake City, Utah

[73] Assignee: Dow Corning Corporation, Midland, Mich.

[21] Appl. No.: 432,005

[22] Filed: Nov. 6, 1989

Related U.S. Application Data

[63] Continuation-in-part of Ser. No. 258,950, Oct. 17, 1988, abandoned.

[51] Int. Cl.$^5$ ................................................ C07F 7/08
[52] U.S. Cl. ..................................................... 556/978
[58] Field of Search ......................................... 556/478

[56] References Cited

U.S. PATENT DOCUMENTS

| | | | |
|---|---|---|---|
| 2,403,370 | 7/1946 | Hurd | 260/607 |
| 2,413,582 | 12/1946 | Rust et al. | 260/607 |
| 2,427,605 | 9/1947 | Hurd | 260/607 |
| 2,626,269 | 1/1953 | Barry | 260/448.2 |
| 2,762,824 | 9/1956 | Brown | 260/448.2 |
| 2,857,414 | 10/1958 | Schmidt et al. | 260/448.2 |
| 2,945,874 | 7/1960 | Jenkner | 260/448.2 |
| 3,065,253 | 11/1962 | Merritt | 260/448.2 |
| 3,480,654 | 11/1969 | Sundermeyer et al. | 260/429.7 |
| 3,666,783 | 5/1972 | LeFort | 556/478 |
| 4,155,927 | 5/1979 | Straussberger et al. | 556/478 |
| 4,158,010 | 6/1979 | Graf et al. | 260/448.2 |
| 4,595,777 | 6/1986 | Bakoli et al. | 556/478 |
| 4,711,966 | 12/1987 | Nelson | 556/478 |

FOREIGN PATENT DOCUMENTS

| | | | |
|---|---|---|---|
| 1162478 | 6/1985 | U.S.S.R. | 556/478 |
| 689486 | 3/1953 | United Kingdom | 556/478 |

OTHER PUBLICATIONS

Hurd, *J. Am. Chem. Soc.* (1945), vol. 67, pp. 1545–1548.

*Primary Examiner*—Paul F. Shaver
*Attorney, Agent, or Firm*—James E. Bittell

[57] ABSTRACT

A process for the preparation of more highly alkylated silanes. The process comprises (A) contacting a halide of silicon, a silane or a disilane, with an alkyl halide in the presence of a metal, such as aluminum, which serves as a halogen acceptor, and a sufficient quantity of a catalyst effective in improving exchange of alkyl groups from the alkyl halide with said halogen atoms of the halide of silicon; (B) reacting the halide of silicon with the alkyl halide in the presence of the metal and the catalyst at a temperature greater than about 150° C. to form the more highly alkylated silanes and a metal halide; and (C) isolating and separating the more highly alkylated silanes.

17 Claims, No Drawings

PREPARATION OF ORGANOSILANES

This is a continuation-in-part of copending application(s) Ser. No. 07/258,950 filed on Oct. 17, 1988, now abandoned.

BACKGROUND OF THE INVENTION

This invention relates to the addition of alkyl groups to halides of silicon to produce more highly alkylated organosilanes. More particularly, this invention relates to an improved process for reacting organohalosilanes with organic halides in the presence of a halide-accepting metal.

In the silicones industry organosiloxanes are prepared from the hydrolysis of organohalosilanes. The predominant starting organohalosilanes are the diorganodihalosilanes which produce diorganopolysiloxane materials utilized in fluids, high-molecular weight linear polymers used in silicone elastomers, and the like. Organohalosilanes are primarily produced by the direct reaction of silicon and organic halides, as first disclosed by Rochow and his co-workers in the 1940's. The direct reaction can be controlled so that the predominant component is the diorganodihalosilane. However, other products of lower commercial value are also produced. These other products include tetrahalosilanes, organotrihalosilanes, and similar more highly halogenated species. It would be advantageous if such highly halogenated species could be efficiently converted to the more useful diorganodihalosilanes. Additionally, the demand for silanes of higher organic content such as triorganohalosilanes is often greater than the supply from the direct reaction.

As an early example of the preparation of organosilicon compounds using metallic reagents, Kipping and Dilthey both demonstrated the alkylation of tetrachlorosilane via reaction with an organomagnesium halide, the well-known Grignard process.

Hurd, J. Am. Chem. Soc. (1945), vol. 67, pp. 1545-1548, and Hurd, U.S. Pat. No. 2,403,370, issued Jul. 2, 1946, disclose the alkylation of tetrachlorosilane and various methylchlorosilanes by passing the vapors of these chlorosilanes together with an alkyl halide over finely divided aluminum, zinc, or other reactive metal at elevated temperatures, 300° to 500° C. Hurd discloses that a reaction occurs under these conditions in which chlorine groups on the chlorosilane are replaced by alkyl groups.

Straussberger et al., U.S. Pat. No. 4,155,927, issued May 22, 1979, discloses a process for preparing trimethylchlorosilane which comprises reacting methyldichlorosilane with methyl chloride and metallic aluminum in the presence of a diatomite. Straussberger et al. neither demonstrates nor suggests the instant invention in which the degree of methyl and chlorine exchange on silicon is maximized.

Turetskaya et al., Soviet Union Patent Publication SU 1162478, published Jun. 23, 1985, shows in examples that an alloy of aluminum with titanium in combination with silicon appears to affect the composition of the product of the reaction of methyl chloride and dimethyldichlorosilane. One cannot conclude that this is an improved catalyst.

SUMMARY OF THE INVENTION

The objective of the instant invention is providing an improved process for the preparation of more highly alkylated organosilanes from the reaction of halides of silicon with an alkyl halide in the presence of a halogen-accepting metal. A further objective of the instant invention is providing a process in which the alkylation of a halide of silicon is effected at an improved rate of production, an increased selectivity toward the more highly alkylated organosilanes, or a combination of both.

The instant invention is based upon the finding that the known process of reacting a halide of silicon with an alkyl halide in the presence of a halogen-accepting metal such as aluminum is significantly improved by the addition of a catalyst. The benefits from the instant invention are, individually or in combination—shortened induction time to reach steady-state alkylation conditions, increased conversion of the reactant halides of silicon and alkyl halide, and increased alkyl efficiency or incorporation of alkyl groups generated from the reacted alkyl halides into the reacted halides of silicon.

The materials effective as a catalyst to achieve the objectives of the instant invention are theorized to be materials which improve contact of the vapors of the reactant alkyl halide and halide of silicon with the halogen-accepting metal by facilitating increased penetration or disruption of a metal oxide film or layer on the surface of the halogen-accepting metal. However, the instant invention is not limited by this theory.

DESCRIPTION OF THE INVENTION

In accordance with the instant invention there is provided a process to increase the number of alkyl groups on silanes under conditions that will be delineated herein. What is described, therefore, is a process for preparing more highly alkylated silanes having the formula, $$R_a R^i_b Si X_{(4-a-b)},$$

wherein each R is independently selected from a group consisting of methyl, ethyl, and n-propyl; each $R^i$ is independently selected from a group consisting of hydrogen atoms, alkyl, substituted alkyl, alkenyl, aryl, and alkaryl groups; a has a value of 1, 2, 3, or 4, b has a value of 0, 1, 2, or 3, and the sum of a+b is 4 or less; and X is an independently selected halogen atom, said process comprising:

(A) contacting a halide of silicon, having the formula, $$R^i_b Si X_{4-b},$$

wherein $R^i$, b, and X are defined above;
with an alkyl halide, having the formula, $$RX,$$

wherein R and X are defined above,
in the presence of a metal which serves as a halogen acceptor and a sufficient quantity of a catalyst effective in improving exchange of said R groups from the alkyl halide with said halogen atoms X of said halide of silicon to yield said more highly alkylated silanes;

(B) reacting the halide of silicon with the alkyl halide in the presence of the metal and the catalyst at a temperature greater than about 150° C. to form the more highly alkylated silanes and a halide of the metal; and (C) isolating and separating the more highly alkylated silane.

The metal which serves as a halogen acceptor can be selected from a group consisting of aluminum and zinc. The preferred metal is aluminum. The metal can be in the physical form, for example, of powders, wire, flake, granules, and chunks. It is preferred that the form of the metal expose as much surface area as possible to facilitate contact with the halide of silicon and the alkyl halide.

For the purposes of the instant invention, "a catalyst effective in improving exchange of said R groups from the alkyl halide with said halogen atoms X of said halide of silicon to yield said more highly alkylated silanes" is a material that provides the benefits, individually or in combination, of (1) shortened induction time to reach steady-state alkylation conditions; (2) increased conversion of the reactant halides of silicon and alkyl halide; and (3) increased overall incorporation of alkyl groups generated from the reacted alkyl halides into the reacted halides of silicon. As an example, as shown in the examples infra, in the reaction of methyl chloride with dimethyldichlorosilane in the presence of aluminum about 50 to 65 mole percent of the methyl groups available for exchange are incorporated in the final methylchlorosilanes. Addition of a catalyst, such as tin metal or a tin compound at levels of greater than about 3000 parts per million, based upon the weight of the aluminum, raises methyl incorporation to as high as 90 mole percent at the same conditions of temperature and contact time.

It is known in the art that certain compounds attack aluminum. Examples of these compounds are hydrogen chloride, magnesium chloride, zinc chloride, phosphorous, and ferric chloride. It is theorized that catalysts that are effective at increasing alkyl/halogen exchange in the above reaction are those materials that improve contact of the vapors of the reactant alkyl halide and halide of silicon with the halogen-accepting metal by facilitating increased penetration or disruption of a metal oxide film or layer on the surface of the halogen-accepting metal. However, the instant invention is not limited by this theory.

The catalyst can include, for example, tin metal and tin compounds, antimony and antimony compounds, aluminum bromide, boron, phosphorous, metal phosphorous alloys, metal phosphides, palladium, iodine, iron chloride, hydrogen halides, copper and copper compounds, and mixtures thereof. In considering aluminum as the halogen-accepting metal, the catalyst can further include mercury, mercury compounds, zinc and zinc compounds. It is understood that the catalyst is not limited to these materials or compounds used as examples. Any material or compound which functions in an equivalent manner to improve contact of the vapors of the reactant alkyl halide and halide of silicon with the halogen-accepting metal by facilitating increased penetration or disruption of a metal oxide film or layer on the surface of the halogen-accepting metal is intended to be encompassed by the instant invention. The preferred catalysts are tin and tin compounds. The most preferred catalyst is tin metal.

"A sufficient quantity of catalyst" varies with the particular catalyst. However, most catalysts are effective at concentrations of greater than about 3000 parts per million (ppm) by weight, based upon the weight of the halogen-accepting metal. The inventors project that amounts lower than 3000 ppm are effective as a catalyst. Thus, it is projected that levels of catalysts of 100 ppm or greater are effective in increasing alkyl/halogen exchange. However, these lower amounts of catalyst are susceptible to inactivation and poisoning by impurities within the process. As shown in the examples, infra, levels of catalysts greater than about 3 percent are effective and appear to have no detrimental effect. The inventors project that higher levels of catalysts can be utilized, but no additional benefit is anticipated.

When copper or copper compounds are used as a catalyst, a preferred concentration is about 3000 to 60,000 ppm copper. Higher concentrations of copper can be employed, but no advantage is perceived. Lower concentrations of copper may also work, but with reduced efficiency of alkyl/halogen exchange. The catalytic activity of copper and copper compounds is improved by the presence of tin, tin compounds, zinc, zinc compounds, and mixtures thereof. A preferred concentration is about 50 to 3000 ppm zinc and/or tin.

The catalyst may be combined with the metal which serves as a halogen acceptor as a heterogeneous mixture of solids. The catalyst may also be combined as an alloy with the halogen accepting metal. The catalyst can be in the physical form, for example, of powders, granules, flakes, chips, or pellets.

The more highly alkylated silanes can be, for example, tetramethylsilane, tetraethylsilane, dimethyldiethylsilane, trimethylchlorosilane, triethylfluorosilane, dimethyldichlorosilane, methyldichlorosilane, diethyldibromosilane, methyltrichlorosilane, ethyldimethylchlorosilane, ethylmethyldichlorosilane, dimethylchlorosilane, dimethylvinylchlorosilane, triethylallylsilane, trifluoropropylmethyldichlorosilane, trifluoropropyldimethylchlorosilane, methylphenyldichlorosilane, and diphenylmethylchlorosilane.

The halides of silicon which will be enriched in alkyl groups are selected from halosilane and organohalosilanes. These materials are represented by the formula, $$R^i{}_b SiX_{4-b},$$

b, and X are defined above. Each $R^i$ can be an alkyl group, for example, a hydrocarbon group containing 1 to 10 carbon atoms; a substituted alkyl group, for example, chloromethyl or trifluoropropyl; an alkenyl group, for example, vinyl, allyl, or hexenyl; or an aryl or alkaryl group, for example, phenyl, tolyl, or benzyl.

The halosilane can be, for example, tetrachlorosilane, tetrafluorosilane, tetrabromosilane, trichlorosilane, tribromosilane, difluorosilane, dichlorosilane, bromosilane, or chlorosilane. The organohalosilane can be, for example, methyltrichlorosilane, ethyltrifluorosilane, methylethyldibromosilane, dimethyldichlorosilane, methyldichlorosilane, methyltrichlorosilane, vinyltrichlorosilane, methylvinyldibromosilane, allyltribromosilane, trifluoropropyltrichlorosilane, trifluoropropylmethyldichlorosilane, phenyltrichlorosilane, or phenylmethyldichlorosilane.

The alkyl halide can be, for example, methyl fluoride, methyl bromide, methyl chloride, ethyl fluoride, ethyl bromide, ethyl chloride, or n-propyl bromide. Methyl chloride and ethyl chloride are preferred alkyl halides.

The molar ratio of the halide of silicon and the alkyl halide fed to the reactor is not critical. The molar ratio can vary depending upon the starting reactants, the desired product, and the reaction conditions. Examples of molar ratios that are utilized are illustrated in the examples, infra.

Contacting the halide of silicon and the alkyl halide in the presence of a metal which serves as a halogen acceptor and the catalyst, can be effected by known means for gas-solid contact. Such contact can be effected by vaporizing the halide of silicon and the alkyl halide and feeding these vapors combined or separately to a vessel containing the solid metal and catalyst. The solids can be configured in such contact arrangements as a packed bed, a stirred bed, a vibrating bed, or a fluidized bed.

To facilitate reaction of the halide of silicon, the alkyl halide, and the metal, a vessel should have provisions to control the temperature of the contact zone. For continuous operation, the vessel should include provisions to replenish the halogen-accepting metal as it is converted to a metal halide.

The temperature in the contact zone to effect reaction should be greater than about 150° C. Preferably, the temperature in the contact zone should be in a range from about 150° to 400° C. More preferably, the temperature should be in a range from about 150° to 250° C. Little reaction is projected to take place at temperatures less than 150° C. Temperatures is excess of 400° C. are not desirable since the rate of cleavage of organic groups from silicon can be significant at these higher temperatures. Additionally, the rate of decomposition of alkyl halides at higher temperatures is also increased.

Residence time of the gaseous halide of silicon and the alkyl halide in contact with the halogen-accepting metal and the catalyst should be greater than about 0.5 seconds. It is preferred that residence time be in a range from about 1 to 15 seconds.

Isolating and separating the more highly alkylated silanes can comprise:

(D) separating metal halide from gaseous more highly alkylated silanes, unreacted halide of silicon, and unreacted alkyl halide; and (E) isolating the more highly alkylated silanes from the unreacted halide of silicon and the alkyl halide.

The metal halide can be a vapor at the conditions of the reaction. Separating the metal halide from the more highly alkylated silanes and remaining reactants can be effected by such known methods as cooling the vapor stream exiting the contact vessel to a temperature low enough to allow recovery of the metal halide as a solid while passing the product silanes and remaining reactants through as a vapor. The metal halides can also remain in the reactor. The vapor stream of gaseous product silanes and remaining reactants can be condensed to a liquid crude product. The more highly alkylated silanes can be isolated in high purity from the remaining reactants by such known methods as distillation.

So that those skilled in the art may better understand and appreciate the instant invention, the following examples are presented. These examples are presented to be illustrative and are not to be construed as limiting the claims as delineated herein.

EXAMPLE 1

(Not within the scope of the instant invention) An apparatus was assembled for the alkylation of organohalosilanes via the reaction of an organohalosilane with an alkyl halide in the presence of aluminum metal. Other than changes in equipment size, this apparatus is typical of that used throughout the subsequent examples.

A carbon steel cylinder approximately 0.75 inch in diameter and capable of being loaded to a height of about 6 inches with solids was filled with aluminum metal. The cylinder was placed in an electrically heated fluidized sand bath to control the temperature of the cylinder and its contents. Feed of reactants to the cylindeer were from the top of the cylinder to the bottom. The aluminum solids were held in place by a plug of glass wool.

Methyl chloride (MeCl) was fed as a gas from a compressed gas cylinder. Methyl chloride flow was controlled by a mass flow meter. The organohalosilane feed, in this case dimethyldichlorosilane ($Me_2$), began as a liquid feed from a positive displacement pump. The MeCl and organohalosilane feeds were passed through approximately 4 feet of coiled stainless steel tubing in the heated fluidized sand bath.

The vapors exiting the reactor passed through a heated trap, temperature controlled at approximately 100° C., to remove $AlCl_3$ from the vapor stream as a solid. The remaining vapors were passed to a cold trap to recover the unreacted MeCl and the resultant methylchlorosilane mixture. The liquid crude product was then analyzed by gas chromatography (GC).

The reactor cylinder was charged with 16.1 g of aluminum powder. The aluminum powder was Alcan 44, atomized aluminum powder, purchased from Alcan-Toyo American, Joliet, Ill. The volume of the reactor filled with aluminum was 10.4 cc. The reactor was heated to a furnace temperature of about 250° C. under a nitrogen purge. $Me_2$ was fed to the vaporizer and the reactor at a rate of 12.3 g/hr. MeCl gas was fed to the reactor at a rate of 8.7 g/hr. The feeds resulted in a $MeCl/Me_2$ mole ratio of 1.81/1. The run was continued for approximately 13 hours. The weight of solids in the reactor at the end of the run was 2.3 g. At the reactor temperature, the reactant gases were calculated to have a residence time of approximately 2.0 seconds at the beginning of the run and a residence time of approximately 0.3 seconds at the end of the run.

Samples of the crude product were taken hourly and analyzed by GC. Table 1 is a summary of these results. The samples are designated in Table 1 as "Time" in hours. The results of crude product analysis is represented by the tetramethylsilane ($Me_4$) and trimethylchlorosilane ($Me_3$) content on a $MeCl/Me_2$-free basis, designated as "%$Me_4$" and "%$Me_3$" in Table 1. Based upon product recovery, feed composition and product analyses, conversion of starting $Me_2$, conversion of MeCl, and percent of MeCl converted that was incorporated in the more highly methylated product chlorosilanes were calculated. These results are reported in Table 1, as "%SiCl Conv", "%MeCl Conv", and "%Me Eff", respectively.

TABLE 1

| Time | % $Me_4$ | % $Me_3$ | % SiCl Conv | % MeCl Conv | % Me Eff |
|---|---|---|---|---|---|
| 1 | 0.0 | 1.0 | 1.2 | 22.5 | —[a] |
| 2 | 0.0 | 0.5 | 1.1 | 0 | —[a] |
| 3 | 0.0 | 0.5 | 1.0 | 0 | —[a] |
| 4 | —[a] | 2.1 | 2.0 | 11.3 | —[a] |
| 5 | —[a] | 24.6 | 0.7 | 15.0 | 0 |
| 6 | 20.0 | 48.1 | 2.8 | 22.9 | 3.8 |
| 7 | 29.1 | 66.0 | 4.3 | 41.4 | 26.5 |
| 8 | 25.8 | 72.0 | 61.4 | 77.5 | 54.6 |
| 9 | 23.8 | 73.6 | 85.1 | 86.4 | 62.5 |
| 10 | 26.7 | 70.5 | 88.6 | 90.8 | 62.6 |
| 11 | 34.9 | 62.1 | 90.8 | 94.0 | 66.2 |
| 12 | 27.7 | 69.2 | 80.6 | 76.0 | 69.6 |
| 13 | 22.4 | 73.1 | 61.5 | 70.9 | 54.4 |

Note:
[a] = Cannot be determined accurately

The above results demonstrate a long induction period to reach steady state and the predominance of Me$_3$SiCl rather than Me$_4$Si in the reaction product when no catalyst is utilized with aluminum in the methylation of methylchlorosilanes.

EXAMPLE 2

Using the apparatus, procedures, and raw materials of Example 1, a run was made in which approximately 5000 ppm of tin metal was added to the aluminum in the reactor. The tin metal was a fine powder of less than about 325 mesh purchased from Belmont Metals.

The run was continued for approximately 8 hours. Table 2 is a summary of the results. The notation utilized in Example 1 is utilized in Table 2.

TABLE 2

| Time | % Me$_4$ | % Me$_3$ | % SiCl Conv | % MeCl Conv | % Me Eff |
|---|---|---|---|---|---|
| 1 | 9.1 | 48.4 | 4.6 | 44.0 | —$^a$ |
| 2 | 57.6 | 37.1 | 75.9 | 86.0 | 64.6 |
| 3 | 62.5 | 34.4 | 96.6 | 97.7 | 73.3 |
| 4 | 76.6 | 21.7 | 99.4 | 97.7 | 83.2 |
| 5 | 77.3 | 21.5 | 99.4 | 97.9 | 84.2 |
| 6 | 80.6 | 18.2 | 99.5 | 96.4 | 86.9 |
| 7 | 65.8 | 30.3 | 94.2 | 86.2 | 82.3 |
| 8 | 29.0 | 69.5 | 61.5 | 38.8 | 93.7 |

Note:
$^a$ = Cannot be determined accurately

The above results demonstrate the beneficial effects of the addition of tin as a catalyst. These benefits are (1) significantly reduced induction period; and (2) significantly improved incorporation of methyl groups into the resulting methylchlorosilanes.

EXAMPLE 3

Using the apparatus, procedures, and materials of Example 1, a run was made in which approximately 4300 ppm of tin phosphide (SnP) was added to the aluminum in the reactor. The run was continued for approximately 8 hours. Table 3 is a summary of the results. The notation utilized in Example 1 is utilized in Table 3.

TABLE 3

| Time | % Me$_4$ | % Me$_3$ | % SiCl Conv | % MeCl Conv | % Me Eff |
|---|---|---|---|---|---|
| 1 | 28.0 | 68.5 | 45.9 | 60.4 | 54.0 |
| 2 | 45.8 | 51.6 | 93.6 | 80.0 | 87.6 |
| 3 | 50.5 | 48.6 | 93.8 | 77.5 | 96.9 |
| 4 | 36.3 | 59.1 | 86.1 | 63.4 | 92.9 |
| 5 | 36.3 | 59.1 | 68.5 | 62.0 | 74.2 |
| 6 | 13.7 | 80.2 | 51.2 | 53.5 | 54.2 |

The above results further demonstrate the benefits of addition of a catalyst to the reaction of alkyl halides with halides of silicon in the presence of a halogen-accepting metal.

EXAMPLE 4

Using the apparatus, procedures, and similar raw materials as used in Examples 1 and 2, two runs were made to evaluate another aluminum sample for the reaction of Me$_2$ with MeCl. The first run was made without the use of a catalyst. The second run was made with the addition of about 4000 ppm tin metal to the aluminum. Both runs were carried out for a period of about 8 hours.

The aluminum metal evaluated was chopped aluminum wire. The aluminum wire was chopped electrical wire purchased from Metal Center, Inc., Louisville, Ky.

In both the uncatalyzed run and the catalyzed run the induction period was 2 hours or less. The catalyzed run reached a steady-state chlorosilane conversion of from about 60 to 70 percent while the uncatalyzed run reached a steady state chlorosilane conversion of only about 15 percent. In both catalyzed and uncatalyzed runs, the efficiency of the MeCl converted to methylchlorosilanes was in a range from about 40 to 80 percent.

EXAMPLE 5

Apparatus and procedures similar to those utilized in the preceding examples were applied to a study to evaluate various materials as potential catalysts for the methylation of Me$_2$.

A larger reactor tube was utilized. The tube was a cylinder about 1 inch in diameter by about 10 inches in length. The reactor was charged with between 100 and 105 g of aluminum. The volume of the reactor filled with aluminum ranged from about 68 to 80 cc. Reaction temperature ranged from about 250° to 255° C. Me$_2$ feed rate was in a range of about 8.2 to 9.5 g/hr. MeCl feed rate was in a range from about 8.1 to 8.6 g/hr. Feeds were continued for a period of time in a range from about 161 to 298 minutes. The mole ratio of MeCl/Me$_2$ was between 2.2/1 to 2.4/1. At the reactor temperature, the residence time for the feed gases ranged from about 13 to 14.5 seconds.

The aluminum used was Alcan 44 aluminum powder. The potential catalysts evaluated were commercially available reagent in the form of powders.

Samples were taken of the total reactor effluent at the end of each run. Table 4 is a summary of the results of the overall runs for each catalyst. These runs are designated as Samples A, B, C, D, E, F, G, H, J, K, L, M, N, P, Q, R, T, and U, respectively. A run made only with aluminum is designated as Sample S. Table 4 identifies each sample by (1) designating the catalyst used, noted as "Catalyst; (2) the quantity of catalyst used in parts per million relative to aluminum, noted as "ppm"; (3) other results are reported using the notation of Example 1.

TABLE 4

| Sample | Catalyst | ppm | % Me$_4$ | % Me$_3$ | % SiCl Conv | % MeCl Conv | % Me Eff |
|---|---|---|---|---|---|---|---|
| A | SnP | 4635 | 99.1 | 0.4 | 97.2 | 98.4 | 90.0 |
| B | AlBr$_3$ | 10369 | 98.8 | 0.4 | 96.9 | 99.7 | 76.6 |
| C | Sn | 38883 | 99.0 | 0.4 | 85.7 | 93.0 | 87.5 |
| D | SnCl$_2$ | 4517 | 94.9 | 4.1 | 89.5 | 99.6 | 79.6 |
| E | Sn | 3993 | 99.0 | 0.3 | 72.9 | 89.5 | 80.3 |
| F | ZnCl$_2$ | 4101 | 83.2 | 14.8 | 91.6 | 83.2 | 89.9 |
| G | B | 4071 | 89.0 | 10.2 | 77.5 | 78.0 | 87.8 |
| H | MgCl$_2$ | 4185 | 56.7 | 11.7 | 80.0 | 76.4 | 80.8 |
| J | P | 5073 | 78.5 | 20.4 | 68.7 | 67.9 | 87.5 |
| K | ZnP$_2$ | 4446 | 47.7 | 49.5 | 90.6 | 89.6 | 63.6 |

TABLE 4-continued

| Sample | Catalyst | ppm | % Me₄ | % Me₃ | % SiCl Conv | % MeCl Conv | % Me Eff |
|---|---|---|---|---|---|---|---|
| L | Pd | 4194 | 95.1 | 4.1 | 34.7 | 53.2 | 68.9 |
| M | Zn | 4271 | 47.3 | 50.1 | 76.4 | 70.9 | 72.5 |
| N | I₂ | 3980 | 31.2 | 63.5 | 88.2 | 86.8 | 61.7 |
| P | FeCl₃ | 4881 | 47.9 | 47.5 | 62.2 | 69.6 | 57.8 |
| Q | KCl | 5356 | 56.8 | 41.4 | 10.4 | 14.3 | 65.9 |
| R | Mg | 4155 | 13.3 | 26.5 | 4.6 | 8.4 | 76.6 |
| S | None | 0 | 43.9 | 54.2 | 22.9 | 33.8 | 50.9 |
| T | Ti | 4165 | 1.0 | 87.8 | 5.5 | —ᵃ | —ᵃ |
| U | Pb | 4161 | 0 | 86.7 | 2.7 | 7.3 | —ᵃ |

Note:
ᵃ = Cannot be determined accurately

The above results demonstrate that many materials provide beneficial effects as catalyst. Additionally, the above results demonstrate that some materials retard the reaction or are poisons.

EXAMPLE 6

Using the apparatus, raw materials, and procedures utilized in Example 5, hydrogen chloride (HCl) gas was evaluated as a catalyst in place of the solid catalysts above.

The reactor tube was filled with 100 g of aluminum. Me₂SiCl₂ and MeCl were fed at rates of 9.0 g/hr and 8.3 g/hr, respectively. HCl gas was fed at 2 g/hr. The reactor effluent was sampled and analyzed as in Example 5. This sample is designated as Sample W. Table 5 is a summary of the results, using the notation as above.

TABLE 5

| Sample | % Me₄ | % Me₃ | % SiCl Conv | % MeCl Conv | % Me Eff |
|---|---|---|---|---|---|
| W | 44 | 54 | 74.7 | 85.5 | —ᵃ |

Note:
ᵃ = Cannot be determined accurately

EXAMPLE 7

The effect of temperature upon the catalyzed reaction of Me₂ with MeCl in the presence of aluminum was studied. Using the apparatus, procedures, and raw materials of Example 4, two runs similar to Sample E of Example 5 were made at temperatures of 154° and 204° C., respectively. These runs are designated as Samples-AA and BB, respectively. The tin content of each run was about 4000 ppm.

Table 6 is a summary of the results of these two runs compared to Sample E. The notation used in Example 1 is used. Additionally, reactor temperature in °C. is denoted as "Temp".

TABLE 6

| Sample | Temp | % Me₄ | % Me₃ | % SiCl Conv | % MeCl Conv | % Me Eff |
|---|---|---|---|---|---|---|
| AA | 154 | 3.4 | 91.4 | 7.2 | 0 | 0 |
| BB | 205 | 84.3 | 14.3 | 62.9 | 61.3 | 94.3 |
| E | 250 | 96.6 | 0.3 | 72.9 | 89.5 | 80.3 |

The above results demonstrate the effect of temperature upon the reaction of a halide of silicon with an alkyl halide in the presence of a halogen-accepting metal and an effective catalyst.

EXAMPLE 8

A run was made in which methyldichlorosilane (MeH) was used as the starting halide of silicon. Apparatus and procedures similar to those utilized in Example 4 were applied.

The reactor was charged with 100.4 g of aluminum. The volume of the reactor filled with aluminum was 64.3 cc. Contact zone temperature was 250° C. MeH feed rate was 9.7 g/hr. MeCl feed rate was 8.2 g/hr. Feeds were continued for a period of 252 minutes. The mole ratio of MeCl/MeH was 1.9/1. At the reactor temperature, the residence time for the feed gases was about 11 seconds.

The aluminum used was Alcan 44 aluminum powder. The catalyst was tin metal. The tin was added to the aluminum powder so that the tin content of the solids was about 4000 ppm by weight.

Samples were taken of the total reactor effluent at the end of the run. Table 7 is a summary of the results of the run. This run was designated as Sample CC. Table 6 summarizes the results of this run using the notation of Example 1.

TABLE 7

| Sample | % Me₄ | % Me₃ | % SiCl Conv | % MeCl Conv |
|---|---|---|---|---|
| CC | 82.0 | 5.1 | 85.0 | 80.7 |

The above results demonstrate that the reaction of methyldichlorosilane with methyl chloride in the presence of aluminum and a tin catalyst results in the formation methylchlorosilanes which are predominantly highly methylated tetramethylsilane.

EXAMPLE 9

A run was made in which Me₂ was used as the starting halide of silicon and the alkyl halide was ethyl chloride (EtCl). Apparatus and procedures similar to those utilized in Example 4 were applied.

The reactor was charged with 101.3 g of aluminum. The volume of the reactor filled with aluminum was 76.0 cc. Contact zone temperature was 250° C. The Me₂ feed rate was 9.3 g/hr. EtCl feed rate was 6.1 g/hr. Feeds were continued for a period of 190 minutes. The mole ratio of EtCl/Me₂ was 1.3/1. At the reactor temperature, the residence time for the feed gases was about 16 seconds.

The aluminum used was Alcan 44 aluminum powder. The catalyst was tin metal. The tin was added to the aluminum powder so that the tin content of the solids was about 4000 ppm by weight.

Crude product was collected and analyzed using the technique of the previous examples. From the results of analyses and a material balance, the following results are reported:

| Crude Product (reported in GC area percent) | |
|---|---|
| EtCl | 11.9 |
| Me₂ | 55.5 |
| (CH₃)₄Si | 2.4 |
| (CH₃)₃SiCl | 17.5 |
| (CH₃)₃(C₂H₅)Si | 5.4 |
| (CH₃)₂(C₂H₅)SiCl | 4.0 |
| (CH₃)(C₂H₅)₂SiCl | 0.6 |
| Chlorosilane conversion | 36.1% |
| Ethyl chloride conversion | 85.8 |

The above results demonstrate that ethyl groups can be incorporated into halides of silanes from the reaction of ethyl chloride with methylchlorosilanes in the presence of aluminum and a catalyst.

EXAMPLE 10

Using the apparatus, procedures, and materials of Example 1, except the organohalosilane feed was methyltrichlorosilane, experiments were conducted in which CuCl alone or in combination with tin was added to the aluminum in the reactor. The runs were continued for approximately 3 hours. The term "ADMEC" refers to additional MeSi per Si fed into the reactor. Other notation is as defined above. Table 8 is a summary of the results.

TABLE 8

| CuCl ppm | Brass ppm | Sn ppm | ADMEC | % SiCl conv. | % Me Eff. |
|---|---|---|---|---|---|
| 0 | 0 | 0 | .148 | 6.2 | 6.5 |
| 0 | 0 | 4000 | .154 | 4.8 | 5.4 |
| 0 | 1500 | 150 | .231 | 8.9 | 19.0 |
| 56,500 | 0 | 0 | .171 | 5.8 | 7.0 |
| 57,800 | 1500 | 0 | .168 | 11.0 | 9.2 |
| 59,700 | 0 | 150 | .256 | 10.0 | 13.5 |
| 62,000 | 1500 | 4000 | .384 | 9.7 | 12.7 |

The results demonstrate the ability of CuCl, in the presence of tin and a halogen-accepting metal, to catalyze the alkylation of organohalosilanes. The results also demonstrate the beneficial effect of tin and zinc when used in addition to copper.

What is claimed is:

1. A process for preparing more highly alkylated silanes having the formula, $$R_aR^i{}_bSiX_{(4-a-b)},$$

wherein each R is independently selected from a group consisting of methyl, ethyl, and n-propyl; each $R^i$ is independently selected from a group consisting of hydrogen atoms, alkyl, substituted alkyl, alkenyl, aryl, and alkaryl groups; a has a value of 1, 2, 3, or 4, b has a value of 0, 1, 2, or 3, and the sum of a+b is 4 or less; and X is an independently selected halogen atom, said process comprising:

(A) contacting a halide of silicon, having the formula, $$R^i{}_bSiX_{4-b},$$

wherein $R^i$, b, and X are defined above; with an alkyl halide, having the formula,

RX, wherein R and X are defined above, in the presence of a metal which serves as a halogen acceptor and a sufficient quantity of a catalyst effective in improving exchange of said R groups from the alkyl halide with said halogen atoms X of said halide of silicon to yield said more highly alkylated silanes;

(B) reacting the halide of silicon with the alkyl halide in the presence of the metal and the catalyst at a temperature greater than about 150° C. to form the more highly alkylated silanes and a halide of the metal; and (C) isolating and separating the more highly alkylated silane.

2. A process according to claim 1, wherein each R is independently selected from a group consisting of methyl and ethyl.

3. A process according to claim 1, wherein the catalyst is a material that improves contact of the vapors of the reactant alkyl halide and the halide of silicon with the halogen-accepting metal by facilitating increased penetration or disruption of a metal oxide layer on the surface of the metal which serves as a halogen acceptor.

4. A process according to claim 1, wherein the catalyst is present as a discrete mixture with the halogen-accepting metal.

5. A process according to claim 1, wherein the catalyst is present as an alloy with the halogen-accepting metal.

6. A process according to claim 1, wherein the metal which serves as a halogen acceptor is selected from a group consisting of aluminum and zinc.

7. A process according to claim 6, wherein the metal which serves as a halogen acceptor is aluminum.

8. A process according to claim 6, wherein the catalyst is selected from a group consisting of tin and tin compounds, antimony and antimony compounds, aluminum bromide, boron, phosphorous, metal phosphorous alloys, metal phosphides, palladium, iodine, iron halides, hydrogen halides, copper and copper compounds, and mixtures thereof.

9. A process according to claim 7, wherein the catalyst is selected from a group consisting of tin and tin compounds, zinc and zinc compounds, antimony and antimony compounds, mercury and mercury compounds, aluminum bromide, iron halides, boron, phosphorous, metal phosphorous alloys, metal phosphides, palladium, iodine, hydrogen halides, copper and copper compounds, and mixtures thereof.

10. A process according to claim 6, wherein the catalyst is selected from a group consisting of tin metal and tin compounds.

11. A process according to claim 10, wherein the catalyst is tin metal.

12. A process according to claim 10, wherein the catalyst is tin phosphide.

13. A process according to claim 1, wherein isolating and separating the more highly alkylated silanes comprises (D) first separating the metal halide from gaseous more highly alkylated silanes, unreacted halide of silicon, and unreacted alkyl halide; and (E) then isolating the more highly alkylated silanes from the unreacted halide of silicon and the alkyl halide.

14. A process according to claim 1, wherein the halide of silicon has the formula, $$(CH_3)_eH_fSiX_{4-e-f},$$

e and f have a value of 0, 1, 2, or 3, respectively, and the sum of e+f is equal to 3 or less; the halogen acceptor is aluminum; and the catalyst is selected from a group consisting of tin metal and its compounds, wherein the catalyst is present at a concentration of greater than about 3000 parts per million, based upon the weight of the aluminum.

15. A process according to claim 14, wherein the halide of silicon is selected from a group consisting of methyltrichlorosilane, dimethyldichlorosilane, and trimethylchlorosilane; wherein the alkyl halide is methyl chloride; the catalyst is selected from a group consisting of tin metal and its compounds; and the halide of silicon, the methyl chloride, the aluminum, and the catalyst are contacted at a temperature in a range from about 150° to 250° C.

16. A process according to claim 1, wherein the halide of silicon has the formula, $$(CH_3)_e H_f SiX_{4-e-f},$$

e and f have a value of 0, 1, 2, or 3, respectively, and the sum of e+f is equal to 3 or less; the alkyl halide is ethyl chloride; the halogen acceptor is aluminum; and the catalyst is selected from a group consisting of tin and its compounds, wherein the catalyst is present at a concentration of greater than about 3000 parts per million, based upon the weight of the aluminum.

17. A process according to claim 16, wherein the halide of silicon is selected from a group consisting of methyltrichlorosilane, dimethyldichlorosilane, and trimethylchlorosilane; wherein the catalyst is tin metal; and the halide of silicon, the ethyl chloride, the aluminum, and the catalyst are contacted at a temperature in a range from about 150° to 250° C.

* * * * *